US00PP21149P2

(12) United States Plant Patent
van Paemel

(10) Patent No.: US PP21,149 P2
(45) Date of Patent: Jul. 6, 2010

(54) ***HELLEBORUS* PLANT NAMED 'ALEXIA'**

(50) Latin Name: *Helleborus×nigercors*
Varietal Denomination: Alexia

(75) Inventor: Thierry van Paemel, Oostkamp (BE)

(73) Assignee: Beekenkamp Plants B.V., Maasdijk (NL)

( * ) Notice: Subject to any disclaimer, the term of this patent is extended or adjusted under 35 U.S.C. 154(b) by 0 days.

(21) Appl. No.: 12/383,845

(22) Filed: Mar. 27, 2009

(51) Int. Cl.
*A01H 5/00* (2006.01)

(52) U.S. Cl. ..... Plt./439

(58) Field of Classification Search ..... Plt./439
See application file for complete search history.

(56) References Cited

OTHER PUBLICATIONS

Upov Plant Variety Database 2009/06. Search for Alexia.*

* cited by examiner

*Primary Examiner*—Annette H Para
(74) *Attorney, Agent, or Firm*—C. A. Whealy

(57) ABSTRACT

A new and distinct cultivar of *Helleborus* plant named 'Alexia', characterized by its upright, outwardly spreading and mounded plant habit; dark green-colored leaves; early and freely flowering habit; long flowering period; and light green-colored flowers.

1 Drawing Sheet

Botanical designation: *Helleborus×nigercors.*
Cultivar denomination: 'ALEXIA'.

CROSS-REFERENCED TO CLOSELY-RELATED APPLICATIONS

Title: *Helleborus* Plant Named 'EMMA'.
Applicant: Thierry van Paemel.
Ser. No: 12/584,855.

BACKGROUND OF THE INVENTION

The present invention relates to a new and distinct cultivar of *Helleborus* plant, botanically known as *Helleborus×nigercors,* and hereinafter referred to by the name 'Alexia'.

The new *Helleborus* plant is a product of a planned breeding program in Oostkamp, Belgium. The objective of the breeding program was to create new vigorous *Helleborus* cultivars with early and freely flowering habit.

The new *Helleborus* plant originated from a cross-pollination conducted by the Inventor in Oostkamp, Belgium in February, 2003 of a proprietary selection of *Helleborus× nigercors* identified as code number 80-0062, not patented, as the female, or seed, parent with a proprietary selection of *Helleborus×nigercors* identified as code number 80-0061, not patented, as the male, or seed, parent. The new *Helleborus* plant was discovered and selected by the Inventor as a single flowering plant from within the progeny of the stated cross-pollination grown in a controlled greenhouse environment in Oostkamp, Belgium in April, 2005.

Asexual reproduction of the new *Helleborus* plant by tissue culture in a controlled laboratory environment in Lochristi, Belgium since May, 2005, has shown that the unique features of this new *Helleborus* plant are stable and reproduced true to type in successive generations.

SUMMARY OF THE INVENTION

Plants of the new *Helleborus* have not been observed under all possible environmental conditions. The phenotype may vary somewhat with variations in environment and cultural practices such as temperature light intensity without, however, any variance in genotype.

The following traits have been repeatedly observed and are determined to be the unique characteristics of 'Alexia'. These characteristics in combination distinguish 'Alexia' as a new and distinct cultivar of *Helleborus:*

1. Upright, outwardly spreading and mounded plant habit.
2. Dark green-colored leaves.
3. Early and freely flowering habit.
4. Long flowering period.
5. Light green-colored flowers.

Plants of the new *Helleborus* differ from plants of the female parent selection in the following characteristics:

1. Plants of the new *Helleborus* are stronger than plants of the female parent selection.
2. Plants of the new *Helleborus* and the female parent selection differ in flower color as plants of the female parent selection have white-colored flowers.

Plants of the new *Helleborus* differ from plants of the male parent selection in the following characteristics:

1. Plants of the new *Helleborus* flower earlier than plants of the male parent selection.
2. Plants of the new *Helleborus* have longer lasting flowers than plants of the male parent selection.

Plants of the new *Helleborus* differ from plants of the *Helleborus* 'EMMA', disclosed in a U.S. Plant patent application Ser. No. 12/584,855 with this application, primarily in flower color as plants of 'EMMA' have white-colored flowers.

Plants of the new *Helleborus* can be compared to plants of *Helleborus* 'Pink Beauty', not patented. Plants of the new *Helleborus* differ primarily from plants of 'Pink Beauty' in the following characteristics:

1. Plants of the new *Helleborus* are more vigorous than plants of 'Pink Beauty'.
2. Plants of the new *Helleborus* have darker green-colored leaves than plants of 'Pink Beauty'.

BRIEF DESCRIPTION OF THE PHOTOGRAPH

The accompanying colored photograph illustrates the overall appearance of the new *Helleborus* plant, showing the colors as true as it is reasonably possible to obtain in colored reproductions of this type. Colors in the photograph may differ slightly from the color values cited in the detailed botanical description which accurately describe the colors of the new *Helleborus* plant.

The photograph comprises a side perspective view of a typical flowering plant of 'Alexia' grown in a container.

DETAILED BOTANICAL DESCRIPTION

The aforementioned photograph and following observations, measurements and values describe plants grown in Maasdijk, The Netherlands in 13-cm containers during the winter in an outdoor nursery and under conditions which closely approximate commercial *Helleborus* production. During the production of the plants, day temperatures ranged from −2° C. to 25° C. and night temperatures ranged from −5° C. to 15° C. Plants had been growing for 17 months when the photograph and the description were taken. In the following description, color references are made to The Royal Horticultural Society Colour Chart, 2001 Edition, except where general terms of ordinary dictionary significance are used.

Botanical classification: *Helleborus×nigercors* 'Alexia'.

Parentage:

*Female, or seed, parent.*—Proprietary selection of *Helleborus×nigercors* identified as code number 80-0062, not patented.

*Male, or pollen, parent.*—Proprietary selection of *Helleborus×nigercors* identified as code number 80-0061, not patented.

Propagation:

*Type.*—By tissue culture.

*Time to initiate roots.*—About 60 days.

*Time to produce a rooted young plant.*—About six months.

*Root description.*—Thick to thin, fleshy; white to brown in color.

*Rooting habit.*—Sparse; moderately branching.

Plant description:

*Plant form and growth habit.*—Herbaceous perennial; upright, outwardly spreading and mounded plant habit; flattened globular; moderately vigorous growth habit.

*Plant height.*—About 19.6 cm.

*Plant diameter (area of spread).*—About 40.8 cm.

Foliage description:

*Arrangement.*—Palmately compound with five leaflets per leaf.

*Leaf length.*—About 14.4 cm.

*Leaf width.*—About 16.4 cm.

*Leaflet length.*—About 12 cm.

*Leaflet width.*—About 4.5 cm.

*Leaflet shape.*—Elliptic to slightly obovate.

*Leaflet apex.*—Acute.

*Leaflet base.*—Attenuate.

*Leaflet margin.*—Serrate.

*Leaflet texture, upper and lower surfaces.*—Smooth, glabrous; leathery.

*Leaflet venation pattern.*—Pinnate.

*Leaflet color.*—Developing leaves, upper surface: Between 139A and 147A. Developing leaves, lower surface: Close to 146A. Fully developed leaves, upper surface: Between 139A and 147A; venation, close to 144A to 144B. Fully developed leaves, lower surface: Close to 147B; venation, close to 152A to 152B.

*Petiole.*—Length: About 13.9 cm. Diameter: About 5 mm. Texture, upper and lower surfaces: Smooth, glabrous. Color, upper and lower surfaces: Close to 146D tinged with close to 176A.

Flower description:

*Flower shape and habit.*—Single rotate flowers arranged in terminal panicles; freely flowering habit, about 31 flowers developing per plant; flowers face upright to outwardly; petals not observed.

*Fragrance.*—Not detected.

*Natural flowering season.*—Long flowering period; plants flower throughout the late winter in The Netherlands.

*Flower longevity on the plant.*—About ten days; flowers not persistent.

*Flower buds.*—Length: About 1.8 cm. Diameter: About 1.3 cm. Shape: Obovate. Color: Close to 145A to 145B.

*Inflorescence height.*—About 19.6 cm.

*Inflorescence diameter.*—About 11.4 cm.

*Flowers.*—Diameter: About 5.5 cm. Depth (height): About 2.3 cm.

*Sepals.*—Arrangement: About five in a single whorl. Length: About 2.7 cm. Width: About 2.4 cm. Shape: Broadly ovate to orbicular. Apex: Rounded. Base: Obtuse. Margin: Entire. Texture, upper and lower surfaces: Smooth, glabrous. Color: When opening, upper surface: Close to 145B. When opening, lower surface: Close to 145C; towards the base, close to 145B. Fully opened, upper surface: Close to 144B; towards the margins, close to 145C; color does not fade with development. Fully opened, lower surface: Close to 145C; towards the center and base, between 145B and 147D.

*Peduncles.*—Strength: Moderately strong. Length: About 14.4 cm. Diameter: About 6 mm. Aspect: About 10° from vertical. Texture: Smooth, glabrous. Color: Close to 146D tinged with close to 176A.

*Pedicels.*—Strength: Moderately strong. Length: About 1.5 cm. Diameter: About 2.5 mm. Aspect: About 35° from the axis of the peduncle. Texture: Smooth, glabrous. Color: Close to 146D tinged with close to 176A.

*Reproductive organs.*—Stamens: Quantity per flower: About 90. Filament length: About 1.1 cm. Filament color: Close to 145D. Anther shape: Reniform; basifixed. Anther length: About 1.5 mm. Anther color: Close to 2B. Pollen amount: Scarce. Pollen color: Close to 2D. Pistils: Quantity per flower: About five. Pistil length: About 9 mm. Stigma shape: Club-shaped. Stigma color: Close to N144A. Style length: About 8 mm. Style color: Close to 145A to 145B. Ovary color: Close to 145A. Nectaries: Quantity per flower: About ten. Length: About 7 mm. Diameter, at apex: About 2 mm. Diameter, at base: About 1 mm Shape: Tubular. Color: Close to N144C. Speeds/fruits: Seed and fruit development have not been observed.

Garden performance: Plants of the new *Helleborus* have been observed to have good garden performance and to tolerate rain, wind and temperatures from about −20° C. to about 35° C.

Pathogen/pest resistance: Plants of the new *Helleborus* have not been shown to be resistant to pathogens and pests common to *Helleborus*.

It is claimed:

1. A new and distinct *Helleborus* plant named 'Alexia' as illustrated and described.

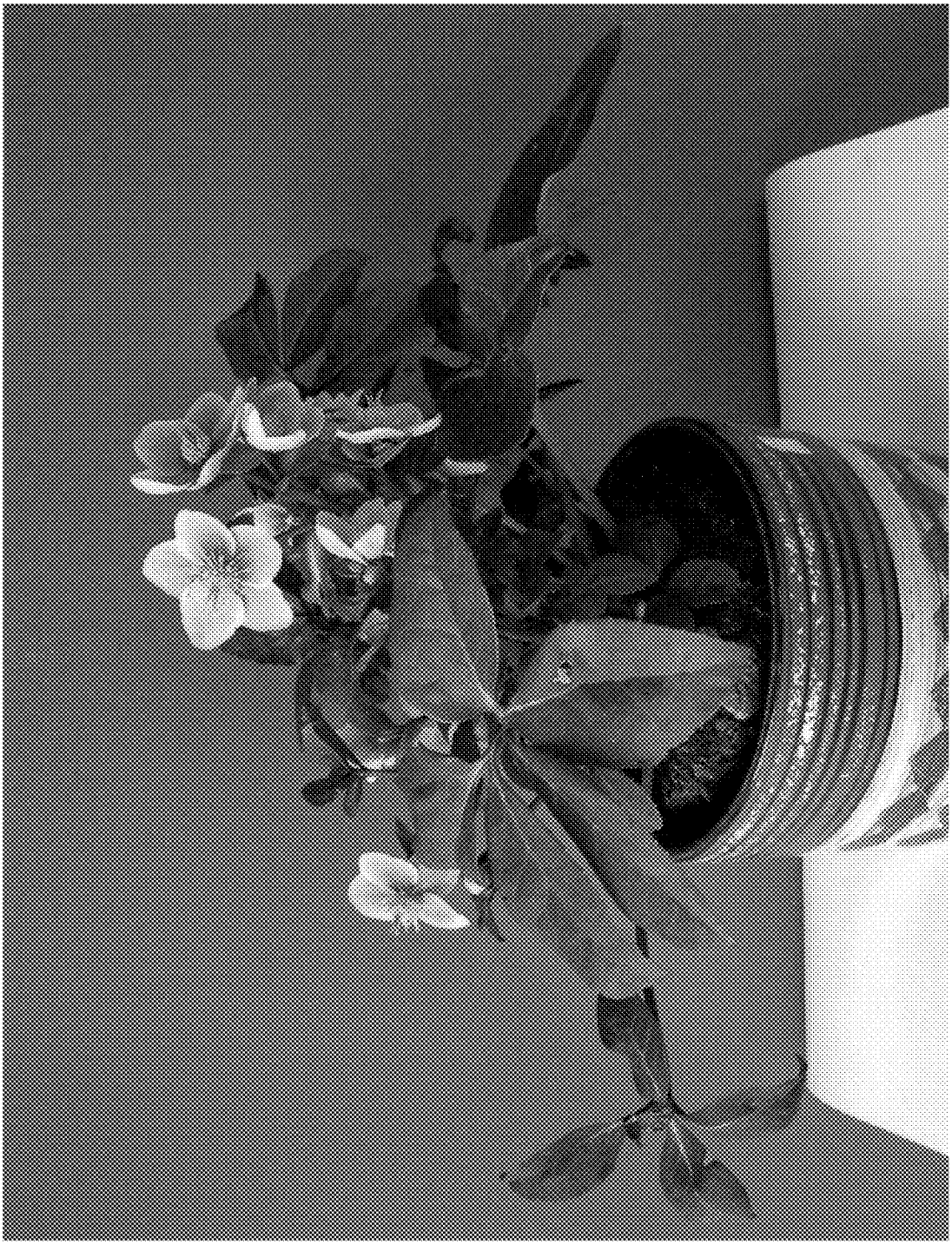

* * * * *